(12) United States Patent
Schiff et al.

(10) Patent No.: US 11,759,146 B2
(45) Date of Patent: Sep. 19, 2023

(54) SENSORY EVOKED DIAGNOSTIC FOR THE ASSESSMENT OF COGNITIVE BRAIN FUNCTION

(71) Applicant: Cornell University, Ithaca, NY (US)

(72) Inventors: Nicholas Schiff, New York, NY (US); Chananel Braiman, New York, NY (US); Chagit Reichenbach, Oak Ridge, TN (US)

(73) Assignee: Cornell University, Ithaca, NY (US)

( * ) Notice: Subject to any disclaimer, the term of this patent is extended or adjusted under 35 U.S.C. 154(b) by 729 days.

(21) Appl. No.: 16/489,982

(22) PCT Filed: Mar. 2, 2018

(86) PCT No.: PCT/US2018/020702
§ 371 (c)(1),
(2) Date: Aug. 29, 2019

(87) PCT Pub. No.: WO2018/160992
PCT Pub. Date: Sep. 7, 2018

(65) Prior Publication Data
US 2020/0237296 A1 Jul. 30, 2020

Related U.S. Application Data

(60) Provisional application No. 62/466,000, filed on Mar. 2, 2017.

(51) Int. Cl.
*A61B 5/00* (2006.01)
*A61B 5/05* (2021.01)
(Continued)

(52) U.S. Cl.
CPC .............. *A61B 5/4821* (2013.01); *A61B 5/05* (2013.01); *A61B 5/377* (2021.01); *A61B 5/378* (2021.01);
(Continued)

(58) Field of Classification Search
CPC ......... A61B 5/4821; A61B 5/05; A61B 5/377; A61B 5/378; A61B 5/38; A61B 5/4088;
(Continued)

(56) References Cited

U.S. PATENT DOCUMENTS 4,844,086 A 7/1989 Duffy
7,471,978 B2 12/2008 John et al.
(Continued)

FOREIGN PATENT DOCUMENTS

WO WO-2017218492 A1 * 12/2017 ............. G06F 3/015

OTHER PUBLICATIONS

Perrin F, Schnakers C, Schabus M, et al. Brain Response to One's Own Name in Vegetative State, Minimally Conscious State, and Locked-in Syndrome. Arch Neurol. 2006;63(4):562-569. doi:10.1001/archneur.63.4.562 (Year: 2006).*

(Continued)

*Primary Examiner* — Colin T. Sakamoto
*Assistant Examiner* — Tommy T Ly
(74) *Attorney, Agent, or Firm* — MCDERMOTT WILL & EMERY LLP

(57) ABSTRACT

The clinical diagnosis and monitoring of patients with neurological conditions may be established through behavioral examinations, assessments or evaluations, or neuroimaging scans. The system and methods described herein diagnose the cognitive function of a subject by measuring the neural response of the subject to one or more naturalistic sensory stimuli. The system measures the subject's sensory evoked response to the naturalistic sensory stimuli by computing the statistical comparison between the subject's neural signal and either the raw stimulus signal or the stimulus' signal envelope. A latency value, or other signal feature, is extracted from the subject's sensory evoked response and a diagnosis of the subject's cognitive function is then made (Continued)

based on the identified latency value or other extracted signal feature.

19 Claims, 7 Drawing Sheets

(51) Int. Cl.
    *A61B 5/38*           (2021.01)
    *A61B 5/377*         (2021.01)
    *A61B 5/378*         (2021.01)

(52) U.S. Cl.
    CPC .............. *A61B 5/38* (2021.01); *A61B 5/4088* (2013.01); *A61B 5/4848* (2013.01); *A61B 5/7246* (2013.01)

(58) Field of Classification Search
    CPC ..... A61B 5/4848; A61B 5/7246; A61B 5/369; A61B 5/37
    See application file for complete search history.

(56) References Cited

U.S. PATENT DOCUMENTS

| | | | |
|---|---|---|---|
| 2008/0167571 A1* | 7/2008 | Gevins | A61B 5/377 600/544 |
| 2009/0062681 A1 | 3/2009 | Pradeep et al. | |
| 2011/0070326 A1* | 3/2011 | Fowler | A23K 20/10 426/87 |
| 2012/0197153 A1* | 8/2012 | Kraus | A61B 5/38 600/545 |
| 2012/0277548 A1* | 11/2012 | Burton | A61B 5/02405 600/559 |
| 2015/0248615 A1 | 9/2015 | Parra et al. | |

OTHER PUBLICATIONS

International Search Report and Written Opinion received in PCT Application No. PCT/US2018/020702, dated May 22, 2018.
International Preliminary Report on Patentability received in PCT Application No. PCT/US2018/020702, dated Sep. 3, 2019.
Abdeltawwab, M. M. (2014). Auditory N1-P2 Cortical Event Related Potentials in Auditory Neuropathy Spectrum Disorder Patients. Journal of International Advanced Otology, 10(3), 270-274.
Abrams, D. A., Nicol, T., Zecker, S., & Kraus, N. (2009). Abnormal cortical processing of the syllable rate of speech in poor readers. The Journal of Neuroscience, 29(24), 7686-7693.
Adler G, Adler J, Schneck M, Armbruster B. 1990. Influence of stimulation parameters on auditory stimulus processing in schizophrenia and major depression: An auditory evoked potential study. Acta Psychiatr Scand 81: 453-458.
Adler G, Gattaz WF. 1993. Auditory evoked potentials in schizophrenic patients before and during neuroleptic treatment. Relationship to psychopathological state. Eur Arch Psychiatry Clin Neurosci 242: 357-361.
Ellger, T., Bethke, F., Frese, A., Luettmann, R. J., Buchheister, A., Ringelstein, E. B., & Evers, S. (2002). Event-related potentials in different subtypes of multiple sclerosis—a cross-sectional study. Journal of the neurological sciences, 205(1), 35-40.
Fein, G., Biggins, C. A., & Mackay, S. (1995). Delayed latency of the event-related brain potential P3A component in HIV disease: Progressive effects with increasing cognitive impairment. Archives of neurology, 52(11), 1109-1118.
Ford JM, Mathalon DH, Kalba S, Marsh L, Pfefferbaum A. 2001. N1 and P300 abnormalities in patients with schizophrenia, epilepsy, and epilepsy with schizophrenialike features. Biol Psychiatry 49: 848-860.
Furdea, A., Halder, S., Krusienski, D. J., Bross, D., Nijboer, F., Birbaumer, N., & Kübler, A. (2009). An auditory oddball (P300) spelling system for brain-computer interfaces. Psychophysiology, 46(3), 617-625.

Giabbiconi, C. M., Dancer, C., Zopf, R., Gruber, T., & Müller, M. M. (2004). Selective spatial attention to left or right hand flutter sensation modulates the steady-state somatosensory evoked potential. Cognitive brain research, 20(1), 58-66.
Horton C, D'Zmura M, Srinivasan R. (2011). EEG reveals divergent paths for speech envelopes during selective attention. International Journal of Bioelectromagnetism 13: 217-222.
Horton, C., D'Zmura, M., & Srinivasan, R. (2013). Suppression of competing speech through entrainment of cortical oscillations. Journal of neurophysiology, 109(12), 3082-3093.
Horton, C., Srinivasan, R., & D'Zmura, M. (2014). Envelope responses in single-trial EEG indicate attended speaker in a 'cocktail party'. Journal of neural engineering, 11(4), 046015.
Howe, A. S., Bani-Fatemi, A., & De Luca, V. (2014). The clinical utility of the auditory P300 latency subcomponent event-related potential in preclinical diagnosis of patients with mild cognitive impairment and Alzheimer's disease. Brain and cognition, 86, 64-74.
Karoumi B, Laurent A, Rosenfeld F, Rochet T, Brunon AM, et al. 2000. Alteration of event related potentials in siblings discordant for schizophrenia. Schizophr Res 41:325-334.
Laurent A, Garcia-Larrea L, d'Amato T, Bosson JL, Saoud M, et al. 1999. Auditory event-related potentials and clinical scores in unmedicated schizophrenic patients. Psychiatry Res 86: 229-238.
Leuthardt, E. C., Schalk, G., Wolpaw, J. R., Ojemann, J. G., & Moran, D. W. (2004). A brain-computer interface using electrocorticographic signals in humans. Journal of neural engineering, 1(2), 63.
Mak, J. N., Arbel, Y., Minett, J. W., McCane, L. M., Yuksel, B., Ryan, D., . . . & Erdogmus, D. (2011). Optimizing the P300-based brain-computer interface: current status, limitations and future directions. Journal of neural engineering, 8(2), 025003.
Müller, M. M., Picton, T. W., Valdes-Sosa, P., Riera, J., Teder-Sälejärvi, W. A., & Hillyard, S. A. (1998). Effects of spatial selective attention on the steady-state visual evoked potential in the 20-28 Hz range. Cognitive Brain Research, 6(4), 249-261.
Phillips, J. M., Maxwell, C. R., Ehrlichman, R. S., & Siegel, S. J. (2009). Event-Related Potentials (ERPs) in the Study of Schizophrenia: How Preclinical ERP Studies have Contributed to our Understanding of Schizophrenia. In Handbook of Neurochemistry and Molecular Neurobiology (pp. 525-543). Springer US.
Schalk, G., & Leuthardt, E. C. (2011). Brain-computer interfaces using electrocorticographic signals. Biomedical Engineering, IEEE Reviews in, 4, 140-154.
Schlor KH, Moises HW, Haas S, Rieger H. 1985. Schizophrenia, psychoticism, neuroleptics, and auditory evoked potentials. Pharmacopsychiatry 18: 293-296.
Schnakers, C., Perrin, F., Schabus, M., Majerus, S., Ledoux, D., Damas, P., . . . & Laureys, S. (2008). Voluntary brain processing in disorders of consciousness. Neurology, 71(20), 1614-1620.
Schreuder, M., Blankertz, B., & Tangermann, M. (2010). A new auditory multi-class brain-computer interface paradigm: spatial hearing as an informative cue. PloS one, 5(4), e9813.
Simpson, T. P., Manara, A. R., Kane, N. M., Barton, R. L., Rowlands, C. A., & Butler, S. R. (2002). Effect of propofol anaesthesia on the event-related potential mismatch negativity and the auditory-evoked potential N1. British journal of anaesthesia, 89(3), 382-388.
Aiken, Steven et al., "Human Cortical Responses to the Speech Envelope," Ear & Hearing 2008, vol. 29, No. 2, 139-157.
Davies, Patricia et al., "Validating the Diagnosis of Sensory Processing Disorders Using EEG Technology," The American Journal of Occupational Therapy 2007, vol. 61, No. 2, 176-189.
Hertrich, Ingo et al., "Magnetic brain activity phase-locked to the envelope, the syllable onsets, and the fundamental frequency of a perceived speech signal," Psychophysiology, 49 (2012), 322-334. Wiley Periodicals, Inc.
Kong, Ying-Yee et al., "Differential modulation of auditory responses to attended and unattended speech in different listening conditions," Hear Res. National Institute of Health, Oct. 2014; 0: 73-81.
Langer, Nicolas et al., "Data Descriptor: A resource for assessing information processing in the developing brain using EEG and eye tracking" CUNY Academic Works, Scientific Data, Apr. 11, 2017.

(56) References Cited

OTHER PUBLICATIONS

Mazzini, Letizia et al., "Long-Latency Auditory-Evoked Potentials in Severe Traumatic Brain Injury," American Congress of Rehabilitation Medicine and the American Academy of Physical Medicine and Rehabilitation, Jan. 2001, vol. 82, 57-65.
Picton, T.W. et al., "Human Auditory Evoked Potentials. II: Effects of Attention," Electroencephalography and Clinical Neurophysiology, 1974, 36: 191-199.
Reichenbach, Chagit S. et al., "The Auditory-Brainstem Response to Continuous, Non-repetitive Speech is Modulated by the Speech Envelope and Reflects Speech Processing," Frontiers in Computational Neuroscience, May 2016, vol. 10, Article 47.
Schulte-Tamburen, A.M. et al., "Comparison of five sedation scoring systems by means of auditory evoked potentials," Intensive Care Med (1999) 25: 377-382.
Trojaborg, W. et al., "Visual and somatosensory evoked cortical potentials in multiple sclerosis," Journal of Neurology, Neurosurgery, and Psychiatry, 1979, 42, 323-330.
Vecchiato, Giovanni et al., "On the Use of EEG or MEG Brain Imaging Tools in Neuromarketing Research," Hindawi Publishing Corporation, Computational Intelligence and Neuroscience, vol. 2011, Article ID 643489, 12 pages.
Benjamin Meltzer et al., "The steady-state response of the cerebral cortex to the beat of music reflects both the comprehension of music and attention," Frontiers in Human Neuroscience, (vol. 9, 6), Aug. 6, 2015.

\* cited by examiner

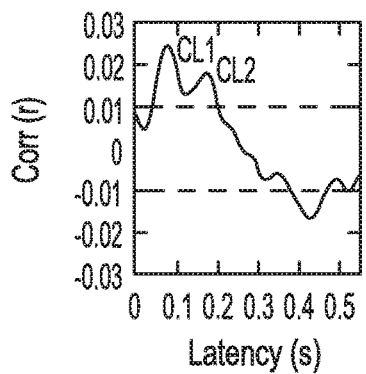 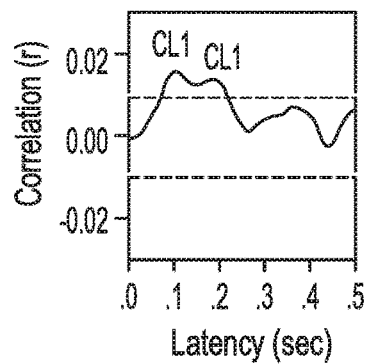
FIG. 3A   FIG. 3B
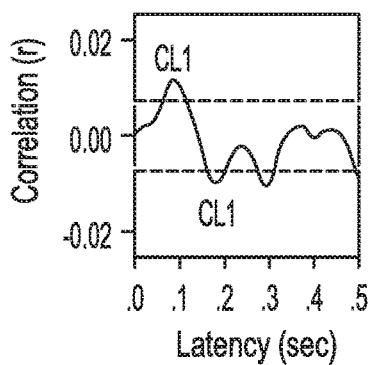 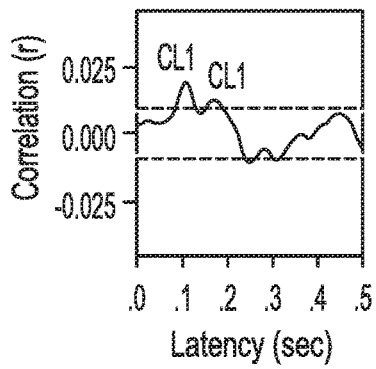 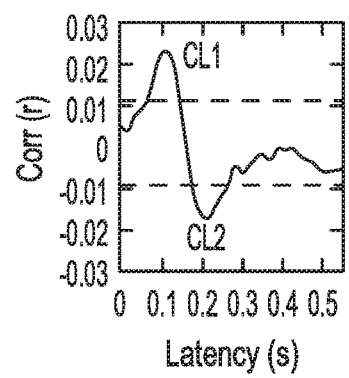
FIG. 3C   FIG. 3D   FIG. 3E
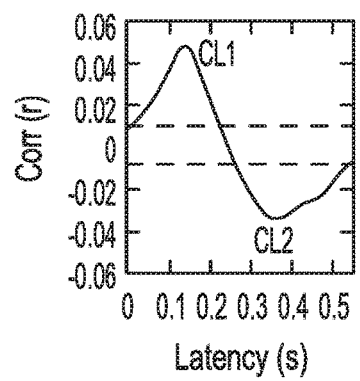 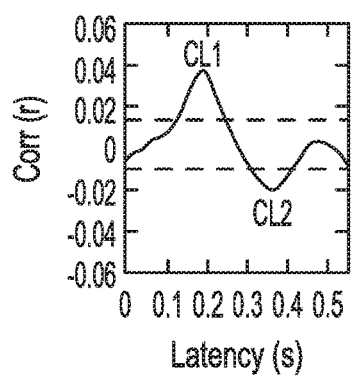
FIG. 3F   FIG. 3G

SENSORY EVOKED DIAGNOSTIC FOR THE ASSESSMENT OF COGNITIVE BRAIN FUNCTION

RELATED APPLICATIONS

The present application is a United States National Phase under 35 U.S.C. § 371 of International Application No. PCT/US2018/020702, filed on Mar. 2, 2018, which claims priority to, and the benefit of, U.S. Provisional Patent Application No. 62/466,000, entitled "A SENSORY EVOKED DIAGNOSTIC FOR THE ASSESSMENT OF COGNITIVE BRAIN FUNCTION" and filed on Mar. 2, 2017, the entire contents of both of which are hereby incorporated by reference for all purposes.

BACKGROUND

The clinical diagnosis and monitoring of patients with neurological conditions may be established through behavioral examinations, assessments, or evaluations. For example, behavioral assessments such as the Coma Recovery Scale (CRS-R) or the Glasgow Coma Scale (GCS) are utilized for diagnosing disorders of consciousness. Behavioral evaluations such as the Functional Systems Scores (FSS) and Expanded Disability Status Scale (EDSS) are utilized for diagnosing multiple sclerosis and the Western Aphasia Battery (WAB) is utilized for diagnosing aphasia. However, behavioral examination may underestimate the cognitive function in patients experiencing motor impairment, covert cognition, and in patients with fluctuations in arousal or reduced motivation.

Imaging modalities such as the positron emission tomography (PET), functional magnetic resonance imaging (fMRI) or computerized tomography (CT) scans may also be used for the diagnosis and monitoring of neurological conditions. For example, in patients with disorders of consciousness, PET and fMRI neuroimaging scans may reveal the preservation of cortical activity and fMRI assessments may demonstrate evidence of command following in patients with disorders of consciousness. However, neuroimaging modalities lack mobility, provide limited temporal resolution, and are not cost effective. An EEG based diagnostic that is as accurate and precise as the imaging modalities has advantages in cost, in the temporal resolution, and in the ease of retesting and monitoring patients.

SUMMARY OF DISCLOSURE

According to one aspect, the disclosure relates to a method for determining the cognitive function of a subject. The method includes receiving, by a processor, a measurement of a neural response of a subject to one or more naturalistic sensory stimuli. The method also includes receiving, by the processor, information related to the one or more naturalistic sensory stimuli, wherein the information includes at least one signal feature of the one or more naturalistic sensory stimuli. The method also includes determining, by the processor, a statistical relationship between the at least one signal feature of the one or more naturalistic sensory stimuli and the measurement of the neural response of the subject. In some implementations, the method of determining the statistical relationship includes cross-correlating at least one signal feature of the naturalistic sensory stimuli with the received measurement of the neural response. The signal feature may be an amplitude envelope of natural speech included within the naturalistic sensory stimuli. The method also includes identifying a latency value based on the determined statistical relationship between the signal feature of the naturalistic sensory stimuli and the measurement of the neural response of the subject. Next, the method includes determining the cognitive function of the subject based on the identified latency value, and outputting the determined cognitive function of the subject. In some implementations, the method may include tracking the determined cognitive function over time.

In some implementations, the naturalistic sensory stimuli may include at least one of auditory, visual, or somatosensory stimuli. In some implementations, the naturalistic sensory stimuli may include natural, conversational speech, continuous video, or continuous somatosensory sensations, or any combination thereof.

In some implementations, the method of determining the cognitive function of the subject incudes classifying the subject as being in a minimally conscious state, having emerged from a minimally conscious state, being in a vegetative state, being in a cognitive motor dissociation command following state, or as being in a healthy state. In some implementations, the method of determining the cognitive function of the subject comprises determining a depth of anesthesia. In some implementations, the method of determining the cognitive function of the subject includes diagnosing a one of speech and language disorder, an auditory processing disorder, a level of Alzheimer's progression, schizophrenia, and a degree of dementia.

In some implementations, the method further includes determining the efficacy of a medical treatment. After administering the treatment, the method includes receiving, by the processor, a measurement of a second neural response of a subject to one or more second naturalistic sensory stimuli. The method also includes receiving, by the processor, information related to the one or more second naturalistic sensory stimuli, wherein the information includes at least one signal feature of the one or more second naturalistic sensory stimuli. Next, the method includes determining, by the processor, a second statistical relationship between the signal feature of the one or more second naturalistic sensory stimuli and the measurement of the second neural response of the subject, and then identifying a second latency value based on the determined second statistical relationship. Based on the second latency value, the method includes determining, by the processor, a second cognitive function of the subject based on the identified second latency value. Next, the method compares the first cognitive function to the second cognitive function and determines an efficacy of the medical treatment based on the comparison. The method outputs the determined efficacy of the medical treatment.

According to one aspect, the disclosure relates to a system for determining the cognitive function of a subject. The system may include one or more stored naturalistic sensory stimuli configured to evoke a neural response of a subject. The system may also include one or more processors implementing a processing unit configured to determine an indication of the cognitive function of the subject to the one or more naturalistic sensory stimuli by, first, receiving a measurement of a neural response in the subject exposed to the one or more naturalistic sensory stimuli. Then the system determines a statistical relationship between the at least one signal feature of the one or more naturalistic sensory stimuli and the measurement of the neural response of the subject. In some implementations, the signal feature of the naturalistic sensory stimuli is a temporal amplitude envelope of the naturalistic sensory stimuli or an amplitude fluctuation of the naturalistic sensory stimuli. In some implementations, the signal feature is an amplitude envelope of natural speech included in the naturalistic sensory stimuli. In some implementations, the system determines the statistical relationship through a cross-correlation analysis between at least one signal feature of the naturalistic sensory stimuli and the received measurement of the neural response. Next, the system identifies a latency value based on the determined statistical relationship between the at least one signal feature of the one or more naturalistic sensory stimuli and the measurement of the neural response of the subject. Next, the system determines an indication of the cognitive function of the subject based on the identified latency value. The system also includes an output module configured to output the determined cognitive function of the subject. In some implementations, the system further includes a storage unit. In some implementations, the processing unit is further configured to store the identified latency value in the storage unit for tracking the determined cognitive function over time.

In some implementations, the naturalistic sensory stimuli may include at least one naturalistic auditory, visual, or somatosensory stimuli. In some implementations, the naturalistic sensory stimuli may include natural, conversational speech, continuous video, or continuous somatosensory sensations.

In some implementations, the system for determining the cognitive function of the subject incudes classifying the subject as being in a minimally conscious state, having emerged from a minimally conscious state, being in a vegetative state, being in a cognitive motor dissociation command following state, or as being in a healthy state. In some implementations, the system of determining the cognitive function of the subject comprises determining a depth of anesthesia. In some implementations, the system for determining the cognitive function of the subject comprises diagnosing a one of a speech and language disorder, an auditory processing disorder, a level of Alzheimer's progression, schizophrenia, and a degree of dementia.

In some implementations, the system may determine an efficacy of a medical treatment. The system for determining the efficacy of a medical treatment may include a first stored naturalistic sensory stimuli and a second stored naturalistic sensory stimuli configured to evoke a neural response of the subject. The system may also include one or more processors implementing a processing unit configured to determine an indication of a second cognitive function of the subject to one or more naturalistic sensory stimuli after the administration of a medical treatment to the subject. After administering the treatment, the system may receive a measurement of a second neural response of the subject to one or more second naturalistic sensory stimuli. The system may receive information related to the one or more second naturalistic sensory stimuli, wherein the information includes at least one signal feature of the one or more second naturalistic sensory stimuli. Next, the system determines a second statistical relationship between the signal feature of the second naturalistic sensory stimuli and the measurement of the subject's second neural response. The system identifies a second latency value based on the second statistical relationship and determines a second cognitive function of the subject based on the identified second latency value. The system compares the first cognitive function to the second cognitive function and outputs the efficacy of the medical treatment based on the comparison.

BRIEF DESCRIPTION OF THE DRAWINGS

The foregoing will be apparent from the following more particular description of example implementations of the invention, as illustrated in the accompanying drawings. The drawings are not necessarily to scale, emphasis instead being placed upon illustrating implementations of the present invention.

FIG. 3A illustrates a plot of a representative individual sensory evoked response for a healthy control.

FIG. 3B illustrates a plot of a representative individual sensory evoked response for a patient presenting as emerged from the minimally conscious state (EMCS), but with evidence of command-following in the functional magnetic resonance imaging paradigm (fMRI CF+).

FIG. 3C illustrates a plot of a representative individual sensory evoked response for a patient presenting as in a minimally conscious state (MCS), but with evidence of fMRI CF+.

FIG. 3D illustrates a plot of a representative individual sensory evoked response for a patient presenting as in a vegetative state (VS), but with evidence of fMRI CF+.

FIG. 3E illustrates a plot of a representative individual sensory evoked response for a patient that emerged from the minimally conscious state (EMCS).

FIG. 3F illustrates a plot of a representative individual sensory evoked response for a minimally conscious state patient (MCS).

FIG. 3G illustrates a plot of a representative individual sensory evoked response for a vegetative state patient (VS).

For purposes of clarity, not every component may be labeled in every figure. The drawings are not intended to be drawn to scale. Like reference numbers and designations in the various figures indicate like elements.

DETAILED DESCRIPTION

The various concepts introduced above and discussed in greater detail below may be implemented in any of numerous ways, as the described concepts are not limited to any particular manner of implementation. Examples of specific implementations and applications are provided primarily for illustrative purposes.

Systems and methods according to the present disclosure provide an electroencephalography (EEG), magnetencephalography (MEG) or electrocorticography (ECOG) based sensory evoked diagnostic for the assessment of brain function in subjects presented with naturalistic sensory stimuli. In some implementations, the naturalistic sensory stimuli may be an auditory stream of speech. The amplitude envelope of speech is one of the most robust features of speech. Example implementations cross-correlate the speech envelope time series of an auditory stream with the neural response of the subject to the auditory stream via EEG, MEG, or ECOG. In example implementations, various signal characteristics of the auditory stream such as amplitude, polarity, latency, and spatial distribution of the peaks of the resultant cross-correlation functions across the EEG, MEG, or ECOG sensors may be used alone, in combination with each other, or as features in with a machine learning algorithm for the diagnosis of neurological disorders, telepathy, and for a touch-free EEG-based computer-brain interface technology.

In some implementations, systems and methods according to the present disclosure provide a diagnostic of the cognitive state of a subject by measuring the sensory evoked response (SER) of the subject to auditory, visual, or somatosensory stimuli.

As used herein, the SER refers to a statistic comparison, for example, a cross-correlation, between a presented stimulus and a patient's EEG, MEG, or ECoG response to that stimulus.

Figure 1:
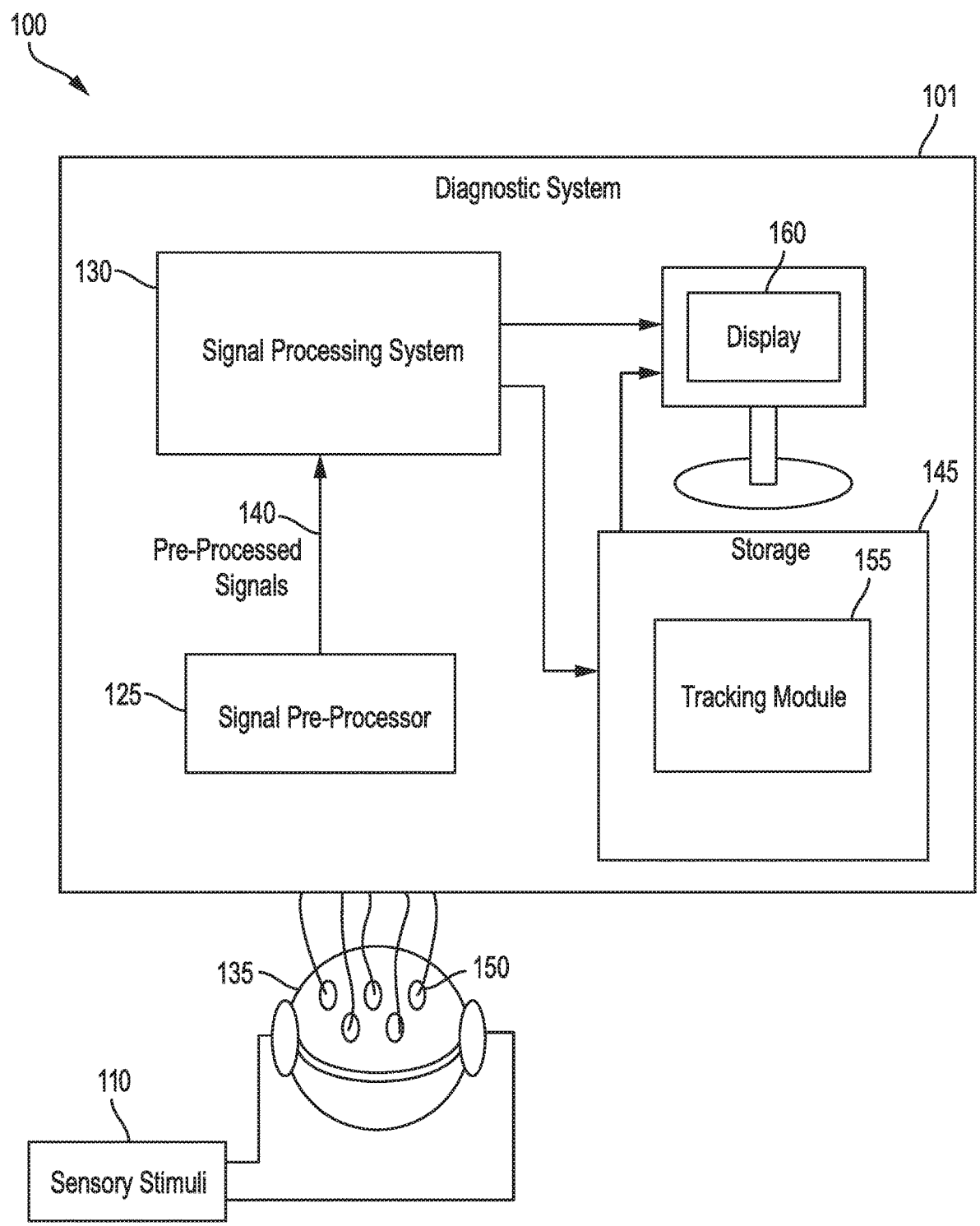
FIG. 1 is a diagram of an environment in which a sensory evoked diagnostic for the assessment of brain function in subjects is provided according to an example implementation.

FIG. 1 is a diagram of an example environment 100 for diagnosing a patient based on a sensory evoked response analysis. FIG. 1 shows a subject 135 presented with a naturalistic sensory stimuli 110. In some implementations, the naturalistic sensory stimuli 110 may be auditory or visual streams or somatosensory input. In FIG. 1, the subject 135 is presented with a stream of naturalistic auditory stimuli via a headset 140. In some implementations, the naturalistic sensory stimuli 110 may be speech, visual images, video, or somatosensory input. In some implementations, the auditory naturalistic stimulus presented to the subject 135 is composed of natural speech. In some implementations, natural speech refers to natural, continuous oral speech. In some implementations, natural speech refers to a spoken dialogue. In some implementations, natural speech refers to the speech having the grammatical and/or diction nuances consistent with spoken language (e.g., as opposed to read aloud language). In some implementations, the naturalistic sensory stimulus is a visual stimulus. The naturalistic visual stimulus may be a continuous, uninterrupted, aperiodic video stream. In some implementations, the naturalistic sensory stimulus is a somatosensory stimulus. The natural somatosensory stimulus may be a continuously varying pressure, vibration, or a thermal (i.e., heating or cooling) sensation. In some implementations, the naturalistic sensory stimuli may be a combination of auditory, visual, and/or somatosensory stimuli. In some implementations, the sensory stimuli signals may be periodic, quasi-periodic or aperiodic signals. Naturalistic stimuli are examples of aperiodic signals.

The environment 100 includes a wearable sensing system 150 such as a wearable EEG sensing system. The sensing system 150 is positioned on the scalp of the subject 135 and acquires the brain signals of the subject 135 in response to the auditory stimulus 110. In some implementations, the sensing system 150 is an EEG, MEG or ECoG based system. In some implementations, the sensing system 150 may have 24 or 7 EEG sensors positioned along the International 10/20 system. The brain signals acquired by the sensing system 150 are amplified, filtered, and digitized via an analog-to-digital converter. The environment 100 includes a diagnostic system 101. The diagnostic system includes a signal pre-processor 125, and a signal processing system 130. The signal pre-processor 125 automatically removes artifacts from the brain signals acquired by the sensing system 150. In some implementations, the signal pre-processor 125 may utilize an independent component analysis (ICA) for artifact removal. In some implementations, artifacts may be removed by visual inspection. In other implementations, values that exceed a certain amplitude may be considered artifacts. The signal pre-processor 125 samples the acquired brain signals at a sampling rate. In some implementations, the sampling rate is equal to or above 250 Hz. Although not shown in FIG. 1, in some implementations, the environment 100 also includes an amplifier, a digitizer, an application programming interface, sensors, and presentation computers or laptops that time-lock the presentation of the sensory stimuli with the acquisition of the neural data. In some implementations, presentation software such as a neurobehavioral system is used to time-lock the presentation of sensory stimuli.

The diagnostic system 101 also includes the signal processing system 130. The signal pre-processor 125 generates pre-processed brain signals 140. The pre-processed. brain signals 140 and the sensory stimuli 110 are input into the signal processing system 130. The signal processing system 130 processes the pre-processed brain signals 140 in order to compute the sensory evoked response of the subject 135 to the sensory stimuli 110. The signal processing system 130 computes the SER and can extract signal features of the SER. The extracted signal features can include the latencies, amplitudes, polarities, and spatial distribution of the SER. As used herein, the spatial distribution of the SER refers to the manner in which the SER varies from EEG channel to EEG channel placed on different locations on the subject's scalp.

The diagnostic system 101 also includes a memory storage unit 145, a tracking module 155, and a display 160. In some implementations, the signal processing system 130 may store data and results in the memory storage unit 145 for offline analysis. In some implementations, the stored data in the memory storage unit 145 may be tracked over time through the tracking module 155. The tracking module 155 may track multiple measurements of the sensory evoked response based on different naturalistic sensory stimuli or different trials of the same naturalistic sensory stimuli over time. In some implementations, the signal processing system 130 may dynamically compute and present the real-time results on the display 160. In some implementations, the results may include the extracted signal features, the classification of the patient condition, and the classification of the working memory, comprehension, and familiarity response. In an operation requiring anesthesia, the real-time results, according to some implementations, may be displayed to reveal the anesthetic depth of a patient. In some implementations, the results may also be actively displayed during a patient screening, in an emergency room setting following severe brain injury, or as a measure to track the patient's recovery and response to existing and novel treatments. For tracking purposes, any of the features of the sensory evoked response, including latencies, amplitudes, polarities, and spatial distribution, may be stored in the storage 145 over time and compared by the signal processing system 130 or tracked by the tracking module 155. The results of the comparison may be displayed on the display 160, for example as a trend line, a graph, or a textual or graphical representation of the comparison results.

The analysis of the subject's cognitive state may be provided by a computer and outputted by the computer for example via the display 160, a printer, or over a computer network. Details describing a suitable architecture for such a computer system are described further in FIG. 7 below.

Figure 2:
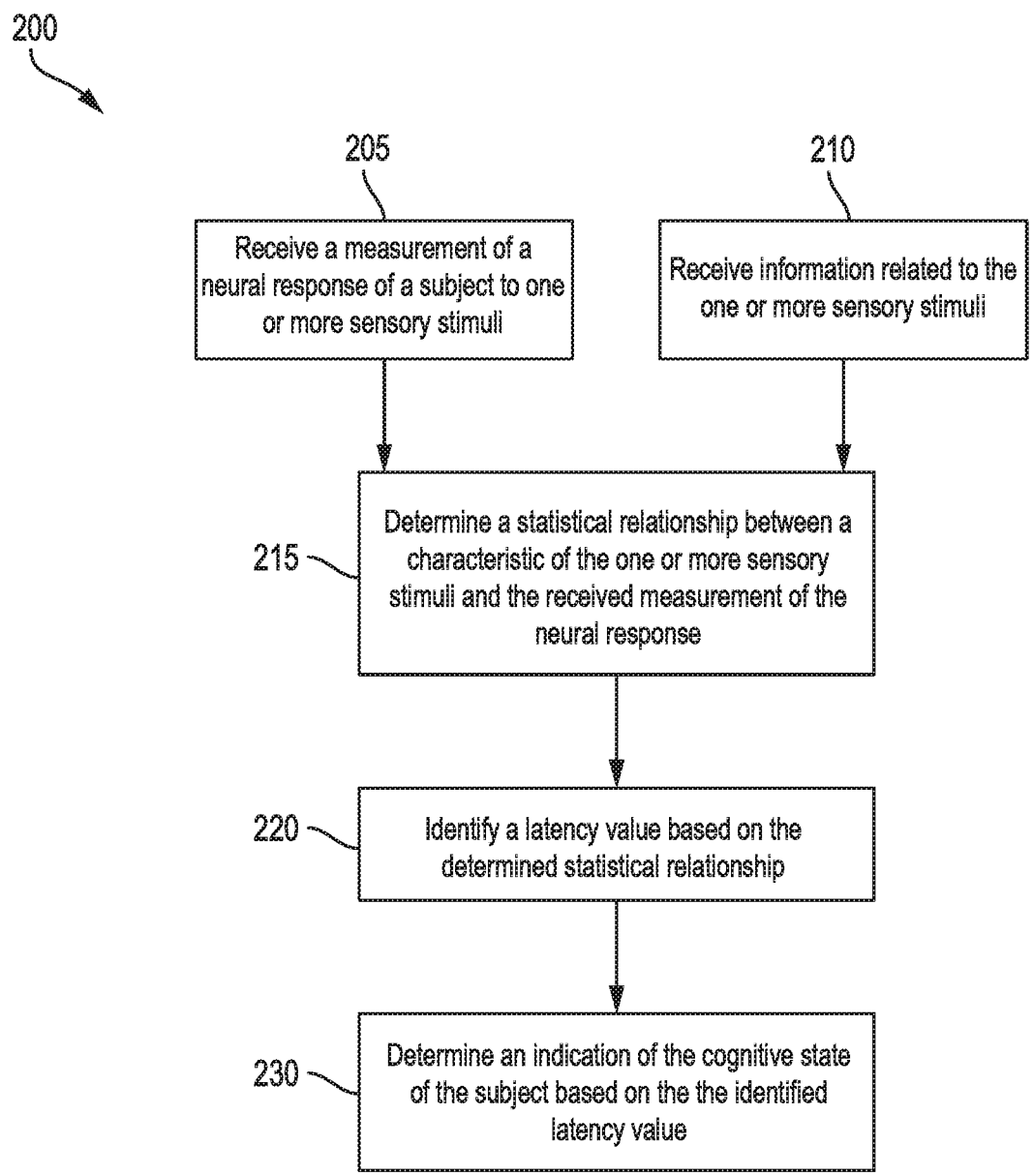
FIG. 2 shows a flow diagram of a method for providing a sensory evoked diagnostic for the assessment of brain function in subjects according to an example implementation.

FIG. 2 shows a flow diagram of an example method 200 for providing a sensory evoked diagnostic for the assessment of brain function according to an example implementation.

Referring back to FIG. 1, the method 200 includes receiving a measurement of a neural response of a subject 135 to one or more sensory stimuli 110 (step 205). The method 200 also includes receiving information related to the one or more sensory stimuli (step 210) that generated the neural response. The method 200 includes determining a statistical relationship between a characteristic of the one or more sensory stimuli and the received measurement of the subject's 135 neural response (step 215) (i.e., an SER signal). The method 200 includes identifying a latency value based on the determined statistical relationship (step 220). The method 200 further includes determining an indication of the cognitive state of the subject based on the identified latency value (step 230). In some implementations, the method 200 can include determining an indication of the cognitive state of the subject based on the values of additional signal features such as amplitude, polarity, and spatial distribution of the sensory evoked response (SER).

Referring to FIGS. 1 and 2, the method 200 includes receiving a measurement of a neural response of a subject such as the subject 135 to one or more naturalistic sensory stimuli 110 (step 205). In some implementations, the naturalistic sensory stimuli may be auditory, visual, or somatosensory input. In some implementations, a naturalistic auditory stimulus is composed of natural, continuous speech. In some implementations, the naturalistic speech may be personally meaningful speech such as family narratives. In some implementations, the amplitude of the naturalistic auditory stimulus may be modulated periodically or occasionally to provide a naturalistic amplitude fluctuation. In some implementations, the naturalistic sensory stimuli may include fluctuations in the visual and somatosensory domains. The fluctuations may include luminosity fluctuations or somatosensory vibrations, pressure, or thermal variations. In some implementations, the contrast or brightness of a visual stimulus may be modulated by a superimposed periodic, quasi-periodic or aperiodic input. A naturalistic video stream is an example of an aperiodic stimulus. In some implementations, somatosensory stimuli may be composed of periodic, quasi-periodic, or aperiodic mechanical vibrations or other somatosensory stimulus.

The method 200 also includes receiving information related to the one or more naturalistic sensory stimuli 110 (step 210) that generated the neural response from step 205. The information can include a digital time series of data representing the naturalistic sensory stimulus time series or a digital or analog signal indicating an amplitude envelope associated with the naturalistic sensory stimuli. In some implementations, the information related to the one or more sensory stimuli may be a natural speech envelope. In some implementations, the information related to the one or more sensory stimuli may be a natural, continuous luminance (or other visual property) envelope.

The method 200 includes determining a statistical relationship between a characteristic of the one or more sensory stimuli from step 210 and the received measurement of the neural response from step 205 (step 215). In some implementations, the sensory stimuli may be composed of predominantly lower frequency components. In some implementations, the sensory stimuli may have a frequency lower than 50 Hz. For sensory stimuli composed of predominantly lower frequencies, the EEG time series is cross-correlated with the sensory input. In some implementations, the sensory time series (for example, a time series corresponding to natural speech) may be composed of predominantly high frequency components with lower modulation frequencies, for example the natural speech envelope. For sensory stimuli composed of high and low or predominantly high frequency components, the sensory envelope is extracted, and the EEG signal and/or the EEG amplitude envelope cross-correlation is computed against the extracted envelope.

The sensory envelope may be determined by computing the magnitude of the Hilbert transform of the sensory stimulus time series. In some implementations, the EEG signal is band-pass filtered in the range of 2-30 Hz. In some implementations, the EEG signal is band-pass filtered in the range of 1-90 Hz. The sensory input and the EEG signal are resampled to have matching sampling rates. The EEG signal and the sensory input from each trial are segmented into epochs and their cross-correlation, r, is computed by the following formula:

$$r = \frac{\Sigma_i[(x(i) - mx) * (y(i-d) - my)]}{\sqrt{\Sigma_i(x(i)-mx)^2}\sqrt{\Sigma_i(y(i-d)-my)^2}}$$

In the formula, y represents the time series of the sensory stimulus input, x represents the EEG signal time series for each channel, my represents the mean of the sensory stimulus input time series, and mx represents the mean of the EEG signal time series. Individual averages are determined by computing the mean of the cross-correlations between the EEG signal time series and the sensory stimulus input time series across all the segments. The sensory evoked response is a signal representing the computed statistical comparison between the EEG signal and the either the raw stimulus signal or the signal envelope.

The statistical significance of the cross-correlations may be ascertained by the following approach. The cross-correlation values for each of the cross-correlation functions for each epoch are randomly redistributed. The mean of the chance cross-correlations is computed and the values in the average random cross-correlation function are grouped across time and channels where the values form an approximately normal distribution. In some implementations, peak values of the cross-correlation function can be compared with control randomized cross-correlations computed by randomly redistributing the values of each cross-correlation segment between, the natural speech envelope and the EEG neural response across the time points, and averaging across the segments. A 95% confidence range of control cross-correlation values can be determined through the mean and standard deviation of the above resultant distribution. Peak values that exceed the natural speech envelope and neural response EEG cross-correlation function that exceed the 95% confidence interval are deemed statistically significant at p≤0.05 following False Discovery Rate multiple comparisons. In some implementations, the standard deviation or standard error of the mean of the sensory evoked response can be computed across multiple segments of cross-correlation functions between the natural speech envelope or other naturalist stimuli and the EEG neural response. Although the statistical relationship described above is a cross-correlation, other types of statistical relationships may also be used. In some implementations, the statistical relationship may be a regression analysis.

Referring back to FIG. 2, next the method 200 includes identifying a latency value based on the determined statistical relationship (step 220). In some implementations, the method 200 may include identifying additional signal features of the sensory evoked response other than latency, such as the polarity, spatial distribution, and amplitudes of the SER step 215, as mentioned above. The cross-correlation of a periodic stimuli with the EEG neural response results in a sensory evoked response composed of a series of recurring peaks whereby the delay of any of the peaks may correspond to the delay of the brain response. The delay between the peaks corresponds to the periodicity of the stimulus and the peak amplitude is the amplitude of the evoked response. For aperiodic input, such as naturalistic speech, the resulting neural response can have multiple peaks with each peak's latency and amplitude corresponding to a neural response to the signal. In some implementations, a cross-correlation analysis of the EEG and the natural speech envelope of healthy subjects reveal peaks at latencies of approximately 90 ms, 20 ms, 320 ms and 450 ms. A similar sensory evoked response may be obtained in the visual and somatosensory modalities with aperiodic naturalistic input.

Next, the method 200 includes determining an indication of the cognitive state of the subject based on the identified latency value from step 220 (step 230). In some implementations, multiple sensory channels and their immediate neighboring electrodes define a region of interest. The various regions of interest are analyzed to determine the region of interest producing the greatest SER magnitude or those that are the best defined (i.e., the SER with the highest magnitude values or those having the most prominent peaks). In some implementations, the signal features of the SER associated with the region of interest producing the highest magnitude or best defined SER response are compared to the standard diagnoses attained from behavioral assessments or imaging modalities. In some implementations, an SER is computed and analyzed for a single predetermined region of the scalp, without comparing multiple regions of interest for a preferred SER signal.

Signal features of the selected SER that are employed as an index or indices of cognitive function can include one or more of the latencies and the delays between peaks, the amplitudes, polarities, and, when multiple regions of interest are evaluated, the spatial distribution of the sensory evoked response. In some implementations, the signal features mentioned above may be input into a machine learning classifier to determine the patient's cognitive state. In some implementations, the sensory stimuli may be presented in a passive paradigm without instructions or working memory, comprehension, familiarity or attention paradigms. In some implementations, the sensory stimuli may be presented in an active paradigm with instructions on working memory, comprehension, or familiarity whereby subjects are instructed to attend to or ignore (inhibit) one or more multiple competing sensory stimuli while focusing on a particular task.

FIGS. 3A-3G illustrate plots of representative individual sensory evoked responses in subjects for patients demonstrating various cognitive states. The CL1 and CL2 peaks of the natural sensory evoked responses response for the individual subjects and their significance in the cross-correlation functions are shown. Cross-correlation values that exceed the dashed lines are significant at p≤0.05 for the control cross-correlation distribution. FIG. 3A illustrates a plot of a representative individual sensory evoked response for a healthy control subject. FIG. 3B illustrates a plot of a representative individual sensory evoked response for a patient for which standard behavior testing suggested the patient had a state of consciousness substantially similar to the emerged from minimally conscious state (EMCS), but which demonstrated command following (a substantially more capable state of consciousness) in the functional magnetic resonance imaging paradigm (fMRI CF+). FIG. 3C illustrates a plot of a representative individual sensory evoked response for a patient for which standard behavior testing suggested the patient had a state of consciousness substantially similar to the minimally conscious state (MCS), but which demonstrated command-following in the fMRI CF+. FIG. 3D illustrates a plot of a representative individual sensory evoked response for a patient for which standard behavior testing suggested the patient had a state of consciousness substantially similar to the vegetative state (VS), but which demonstrated command-following in fMRI CF+. FIG. 3E illustrates a plot of a representative sensory evoked response for a patient in the EMCS state. FIG. 3F illustrates a plot of a representative sensory evoked response for a MSC patient. FIG. 3G illustrates a plot of a representative individual sensory evoked response for a VS patient.

As further demonstrated in FIG. 4, FIGS. 3A-3E illustrate how the SER responses of patients having different cognitive states have different latency values, demonstrating that such latency values can be used to diagnose the state of consciousness of such patients. Specifically, the latency of the first peak (CL1) and second peak (CL2) (and any other CL component) indicates the delay at which the brain processes the stimulus. In a healthy control patient (FIG. 3A), the latency value of the first peak is about 0.08 s. In the EMCS patient, the latency of the first peak is about 0.1 s. In the MCS patient, the latency of the first peak is about 0.15 s, and the latency of the first peak for the VS patient is about 0.2 s. Therefore, the figures indicate that as cognitive function decreases the determined latency value increases because it takes longer for the brain to process the naturalistic stimuli in patients with lower cognitive function.

Further, FIGS. 3B-3D illustrate plots of representative individual natural speech envelope SER signals for patients that presented as EMCS, MCS, or VS but showed evidence of command-following in the functional magnetic resonance imaging paradigm (fMRI CF+), which suggests a higher level of consciousness. In FIG. 3B, the latency value of the first peak demonstrates is about 0.9 which represents a relatively preserved level of cognition, quite similar to that of a healthy control. FIG. 3C illustrates a plot of a representative individual natural speech envelope SER signal for a patient that presented as MCS, but who showed evidence of command-following in fMRI CF+, suggesting a higher level of cognition similar to the patient in FIG. 3B. Similarly, FIG. 3D illustrates a plot of a representative individual natural speech envelope SER response for a patient that presented as VS, but who showed evidence of command-following in the fMRI CF+, which suggests a higher level of cognition not shown in a clinical evaluation, similar to the patients in FIG. 3B and FIG. 3C. The patients' evidence of command-following in the fMRI illustrates a level of covert cognition, not otherwise shown with a clinical evaluation. The sensory evoked response of the patients illustrates how a speech envelope SER evaluation system can diagnose a patient otherwise presenting in the EMCS, MCS, or VS states as having a command following capability absent access to fMRI evaluations. FIGS. 3B-3D and FIG. 4 demonstrates that when command following capability is absent, patients with covert cognition as measured by fMRI responses can also be identified in patients otherwise presenting as in the EMCS, MCS or VS states based solely on behavior analysis.

Figure 4:
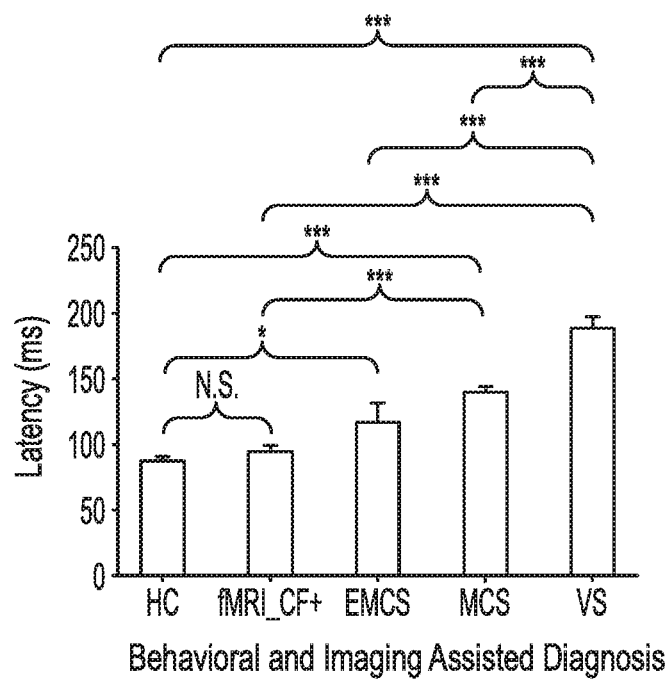
FIG. 4 illustrates latencies of sensory evoked responses in patients of various states, where the state has been determined using behavior diagnosis with assistance from fMRI imaging data.
Figure 4:
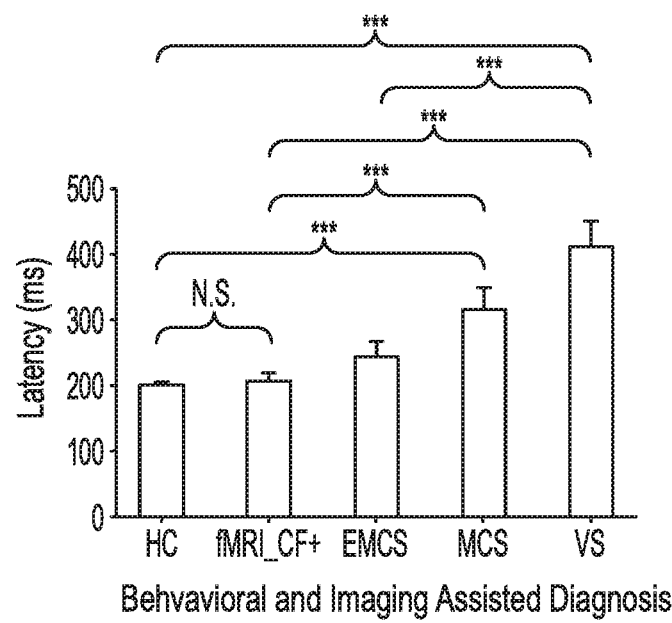

FIG. 4 illustrates groupings of SER latencies obtained in response to natural speech stimulus in relation to multiple healthy control and cognitively impaired patients. FIG. 4 groups patients into five categories: healthy control (HC) patients, patients demonstrating a consciousness disorder based on a behavior diagnosis but who demonstrate command following in the tMRI paradigm (fMRI CF+), patients in the EMCS state (EMCS), patients in the MCS state (MCS), and patients in the vegetative state (VS). In disorders of consciousness, it has been found that the latencies of the components of the naturalistic auditory sensory evoked response are delayed with progressing severity of the behavioral diagnosis. In FIG. 4, the asterisks denote the significance level of the latency differences of the CL1 and CL2 natural speech envelope response components across the patient and healthy control groups by the following:

*=P≤0.05,

***=P≤0.001,

N. S.=Not Significant,

*=P≤0.01.

FIG. 4 illustrates the differences between mean and the standard error of the mean of the latencies for the CL1 and CL2 components of the natural speech SER signal for HC patients and fMRI CF+ patients are not statistically significant. At the same time, FIG. 4 demonstrates that the differences between the CL1 and CL2 latencies of such patients and those of patients in the EMCS, MCS, and VS states that do not demonstrate command following in the fMRI paradigm are statistically significant. For example, the mean value of CL1 latencies for VS patients is about 190 ms, whereas the mean value of CL1 latencies for MCS patients is about 145 ms. The mean value of CL1 latencies for EMCS patients is about 125 ms, whereas the mean value for HC is about 80 ms and the mean CL1 latencies fMRI CF+ patients is about 90 ms. The degree of statistical significance between the HC and fMRI CF+ states and each of the EMCS, MCS, and VS states shown in FIG. 4 demonstrates that natural speech SER signal latencies can be used to effectively distinguish between patients in these various states of consciousness without the need for fMRI or other imaging modalities.

Figure 5:
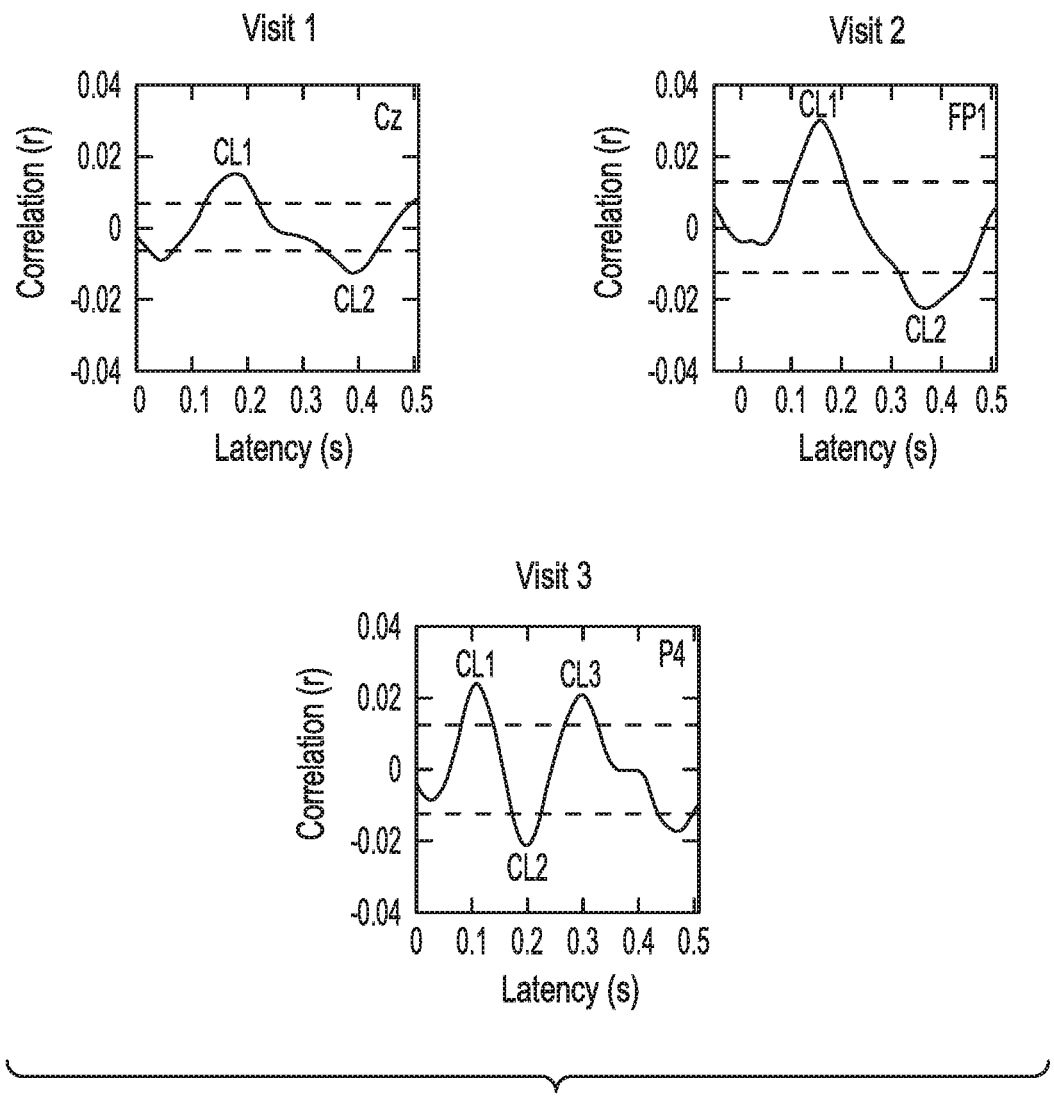
FIG. 5 illustrates a sensory evoked response of a patient at three different stages during a recovery period.

In some implementations, the current systems and methods may be used to track the cognitive function of a patient over time. For example, FIG. 5 illustrates the natural speech envelope SER of a patient at three different stages during a recovery period. The three time points are Visit 1, Visit 2, and Visit 3, where Visit 1 occurred in April, Visit 2 occurred in May, and Visit 3 occurred in June, all of the same year. At the time of Visit 1, the patient was in the MCS. The CL1, CL2 and CL3 peaks of the natural speech envelope sensory evoked response for each time point for the subject and the significance in the cross-correlation functions are labeled. As previously mentioned, it has been found that the latencies of the components of the natural speech envelope SER are delayed with progressing severity of the behavioral diagnosis. Concomitantly, such latencies decrease during a patient's recovery. For example, FIG. 5 shows that at Visit 1, the latencies of the components of the natural speech envelope SER are significantly delayed indicating the severity of the behavioral diagnosis of the patient. As the patient recovers, the natural speech envelope SER of the patient at Visit 2 and Visit 3 each show a reduction in the peak latency values. That is, as the patient recovers, the delays of the natural speech envelope SER shorten. At Visit 3 the patient had recovered to a normal cognitive function, and the delays between peak latencies can be seen to be similar to that of a healthy patient, as shown in FIG. 3A and FIG. 4. The systems and methods of the current disclosure may be used to track the prognosis of a patient who suffered from a brain injury that impaired their cognitive function. For example, a patient's natural speech envelope SER latencies can be tracked over time to determine whether the latencies are decreasing. Decreases in latency suggest improvement in consciousness, whereas unchanging latency values or increasing latency values may demonstrate a lack of change or a worsening condition, respectively.

EXAMPLE APPLICATIONS

The systems and methods disclosed herein may be applied to various applications without departing from the spirit of the disclosure. The forgoing applications and implementations are therefore to be considered in all respects illustrative, rather than limiting of the invention. In some implementations, the signal envelope sensory evoked response (SER) signal and the signal steady state response may be used together to develop EEG, MEG, and ECOG based diagnostics for assessing the brain function of subjects. In some implementations, systems and methods according to the present disclosure provide clinical diagnostics of conditions such as disorders of consciousness following traumatic or ischemic brain injury, the operative monitoring of anesthesia, the evaluation of speech and cognitive function in patients with strokes and aphasia, the diagnosis and tracking of the progression of multiple sclerosis and diabetic neuropathy, the evaluation of novel or existing treatments and pharmacological drugs for neurological conditions, and a diagnostic to evaluate sports or military related brain-injury.

Figure 6:
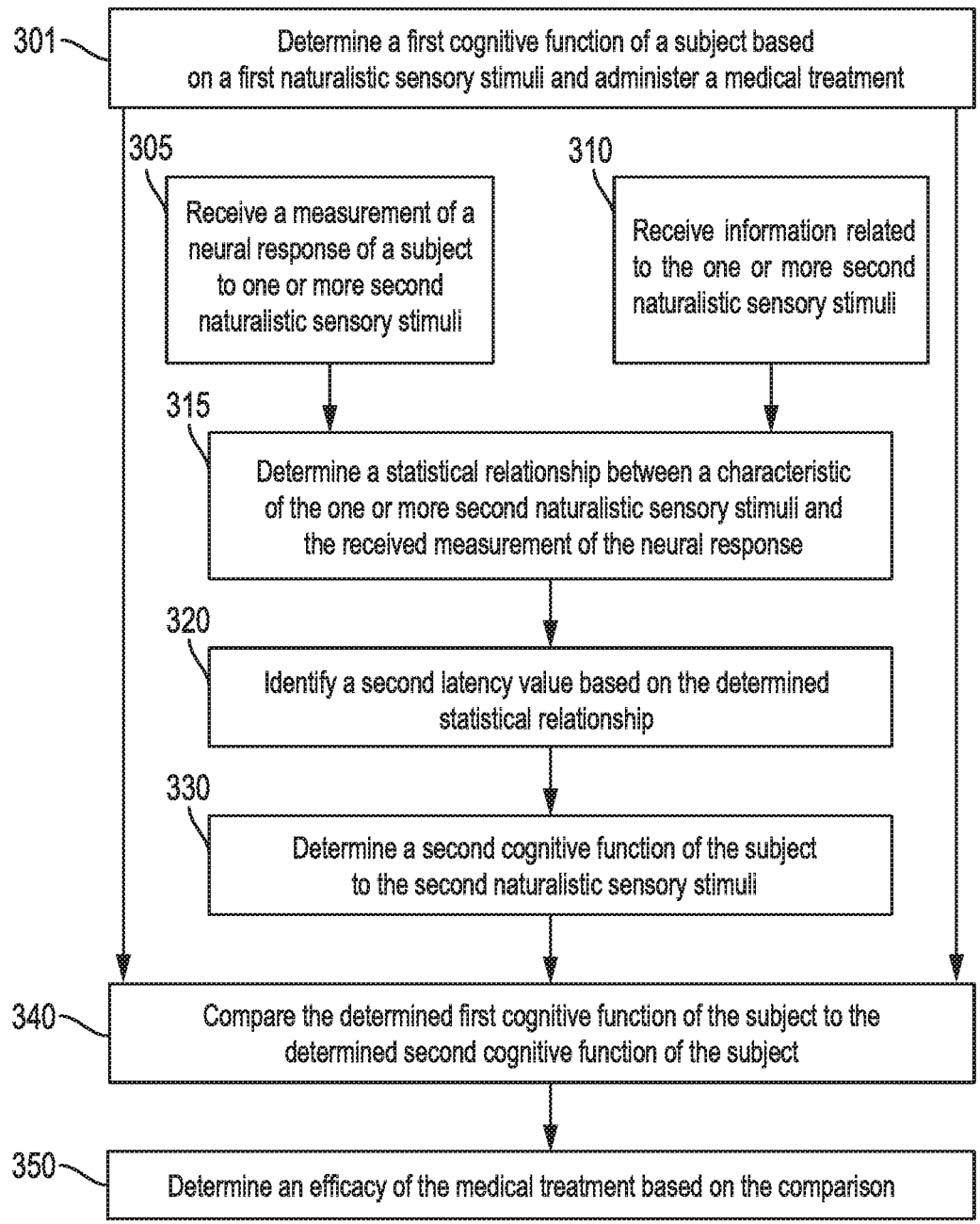
FIG. 6 shows a flow diagram of an example method for determining the efficacy of a medical treatment based on a subject's determined cognitive function.

In some implementations, measuring the sensory evoked response to auditory, visual or somatosensory stimuli may be utilized for the assessment of the efficacy of treatments for neurological conditions. Referring to FIG. 2, FIG. 6 shows a flow diagram of an example method 300 for determining the efficacy of a medical treatment based on a subject's determined cognitive function. First, method 300 includes determining a first cognitive function of a subject based on a first naturalistic sensory stimulus and administering a medical treatment (step 301). Next, method 300 includes receiving a measurement of a sensory evoked neural a measurement of a sensory evoked neural response of the subject to one or more second naturalistic sensory stimuli (step 305). The method 300 also includes receiving information related to the one or more second naturalistic sensory stimuli (step 310). Similar to step 215 in FIG. 2, method 300 also includes determining a statistical relationship between a characteristic of the one or more second naturalistic sensory stimuli and the received measurement of the neural response to the stimulus (step 315). Similar to the method 200 in FIG. 2, method 300 also includes identifying a latency value based on the previously determined statistical relationship from step 315 (step 320). Next, method 300 includes determining a second cognitive function of the subject based on the second naturalistic sensory stimuli (step 330A). Next, method 300 includes comparing the determined first cognitive function of the subject from step 301 to the determined second cognitive function of the subject (step 340). Then, method 300 includes determining an efficacy of the medical treatment from step 301 based on the comparison from step 340 (step 350).

In step 301, method 300 includes determining the first cognitive function of a subject based on the first naturalistic sensory stimuli. In some implementations, the method of determining the first cognitive function may be similar to methods described in FIG. 2 above.

Next, method 300 includes receiving a measurement of a neural response of the subject to one or more second naturalistic sensory stimuli (step 305) and receiving information related to the one or more second naturalistic sensory stimuli (step 310). As mentioned above, the naturalistic sensory stimuli may be an auditory naturalistic stimulus composed of natural speech. In some implementations, the natural speech refers to natural, continuous oral speech. In some implementations, the naturalistic sensory stimulus is a visual stimulus. The naturalistic visual stimulus may be a continuous, uninterrupted video stream. In some implementations, the naturalistic sensory stimulus is a somatosensory stimulus. The natural somatosensory stimulus may be a continuously varying pressure, vibration, or varying thermal sensation. In some implementations, the naturalistic sensory stimuli may be a combination of auditory, visual, or somatosensory stimuli. In some implementations, the sensory stimuli signals may be periodic, quasi-periodic or aperiodic signals. Naturalistic auditory, visual or somatosensory stimuli are examples of aperiodic signals. In some implementations, method 300 may include presenting the first naturalistic sensory stimuli and the second naturalistic sensory stimuli from the same stimulus device. In some implementations, method 300 may include presenting the first naturalistic sensory stimuli and the second naturalistic sensory stimuli from different stimulation devices.

Next, method 300 includes determining a statistical relationship from between a characteristic of the one or more second naturalistic sensory stimuli presented in step 310 and the received measurement of the neural response from step 305 (step 315), then using the determined statistical relationship from step 315 to identify the second latency value (step 320). The sensory evoked response is a signal representation of a statistical comparison between the EEG and either the raw stimulus signal or the signal envelope.

As described above in FIG. 2, the statistical relationship may be a cross-correlation analysis. In some implementations, the statistical relationship may be a regression analysis. For periodic stimuli the latency of any of the peaks, as measured in step 320, indicates the delay the brain processes the naturalistic sensory stimuli. For aperiodic stimuli the latency of each peak, as measured in step 320, indicates the delay that the brain processes the naturalistic stimuli. Then, similar to step 230 in FIG. 2, method 300 includes determining a second cognitive function of the subject to the second naturalistic sensory stimuli.

Method 300 includes comparing the cognitive function determined in step 301 to the cognitive function determined in step 330 (step 340). The cognitive function of the subject is based on the signal features of the sensory evoked response, including the latencies and/or delays between the peaks, the amplitudes, the polarities, and the spatial distribution of the sensory evoked response. Method 300 includes determining the efficacy of the medical treatment based on the comparison in step 340 (step 350). In some implementations, the cognitive function of the subject may improve over time after the administration of the medical treatment. In some implementations, the cognitive function may not improve over time after the administration of a medical treatment, for example as indicated by a decreasing or increase CL1 latency (or any other CL component). In some implementations, the medical treatment may be administering a novel drug where the current method 300 determines the efficacy of the novel drug on the subject through measurements of the subject's sensory evoked response. For example, the novel drug may target aphasia. In some implementations, the SER from method 300 may be utilized as a neural marker of drug efficacy. In some implementations, method 300 may be utilized as a marker of drug efficacy for neurological conditions to guide the progression of clinical trials and drug development in pre-clinical stages by tracking the efficacy of the novel drug over time. In some implementations, neural markers of drug efficacy may inform drug development for neurological diseases. For example, drugs or medical interventions may be advanced or limited based on neural measures before larger and more expensive clinical trials. In addition, neural markers may identify patients that will be most responsive to certain therapies. A neural marker based on the most robust feature of naturalistic speech stimuli can serve as a more sensitive and specific measure of therapeutic efficacy to support the development of new or existing drugs for neurological disorders.

In some implementations, the use of the proposed systems and methods for providing a sensory evoked diagnostic for the assessment of cognitive function in brain injured patients may occur in an outpatient screening, neuro-intensive care unit (ICU), chronic care facilities, primary care settings, or sports and military centers. In some implementations, the system and methods of the current disclosure can track the cognitive function of patients in the operating room of hospitals. The sensory evoked response can be tracked via EEG during an operation requiring sedation by tracking the patient's cognitive function throughout the course of the sedation based on their response to the naturalistic sensory stimuli. In some implementations, systems and methods according to the present disclosure can provide an EEG based diagnostic for intensive care unit monitoring. In the intensive care unit, the current system and methods can monitor and diagnose a severely brain-injured patient's cognitive function and track their prognosis over time. For example, coma patients with a preserved sensory evoked response to a naturalistic sensory stimulus may have an improved outcome compared to patients without a preserved sensory evoked response to a naturalistic sensory stimulus. Similarly, in some implementations, the systems and methods according to the present disclosure provide an EEG or ECoG based diagnostic of cognitive brain function for anesthetic depth and operative monitoring. In some implementations, the sensory evoked response to naturalistic sensory stimuli, such as the natural speech envelope, can be modulated during anesthesia to determine a more sensitive and specific index of anesthetic depth. In some implementations, the natural speech envelope sensory evoked response can also provide real time monitoring of structural integrity of the cortical structures involved in language processing during surgical operations while the patient is under anesthesia by tracking the latency values of the sensory evoked response of cortical structures to naturalistic auditory stimuli.

In some implementations, the current systems and methods can track the expressive language system in patients. The expressive language system may not be recognized in some patients and tracking the reestablishment of inner speech is an important potential biomarker in patient recovery. Inner speech, which is estimated to occur for as much as 25-30% of the wakeful day in healthy adults provides an intrinsically generated, frontal language-related network activation pattern. Thus, using the sensory evoked response and methods of electrophysiological signal identification for language elements, the current systems and methods can be used to measure the restoration of inner speech by tracking the latencies between peaks of the sensory evoked response after the subject receives a naturalistic sensory stimulus over time. As the latencies decrease over time, the patient may be reestablishing their inner speech and their expressive language system.

In some implementations, systems and methods according to the present disclosure provide an EEG, MEG or ECoG based diagnostic of neurological disorders. In some implementations, the neurological disorder may be the result of a traumatic brain injury or ischemic severe brain-injury, such as a stroke. The envelope response in severely brain-injured patients to naturalistic sensory stimuli indicates that the latency of the response is delayed according to the severity of the brain-injury. The preservation of the sensory evoked neural response may be an index of preserved cognitive function and cognitive reserve. In some implementations, the current systems and methods may be used to diagnosis the severity of a patient's neurological disorder and track the disorder over time after the administration of a medical treatment, as shown in FIGS. 2 and 6.

In some implementations, systems and methods according to the present disclosure can provide on-site diagnostics in military applications. A natural auditory envelope-based diagnostic may investigate cognitive function in wounded military service member after injuries incurred on the battlefield. The current systems and methods can help diagnose the severity of the brain injury before the patient is transported to a hospital.

In some implementations, systems and methods according to the present disclosure provide an EEG based diagnostic for sports and athletics applications. A sensory evoked response based diagnostic may investigate cognitive function following repeated or individual instances of head collisions in contact sports and athletics. The current methods can assess the cognitive state of a patient before and after sports events. In some implementations, the current systems and methods track the cognitive function of patients after a sports related brain injury. Referring to FIG. 6, in some implementations, the current systems and methods can determine the efficacy of medical treatment after a patient sustains a concussion from a sports injury. In some implementations, the current systems and methods can track a subject's cognitive function in real time as an EEG-based sensor embedded in a helmet.

In some implementations, systems and methods according to the present disclosure can provide a diagnostic for speech and language impairment disorders. In some implementations, the speech and language impairment may be aphasias. The natural speech envelope is essential for speech comprehension and intelligibility. The sensory evoked response of the natural speech envelope can determine an index of speech impairment based on the latency value determined by the systems and methods disclosed herein. For example, subjects with reading impairments may have a prolonged latency based on the measurement of their sensory evoked response to a naturalistic auditory stimuli compared to good readers. In addition, the amplitude or precision of the envelope response may be atypical in a compressed naturalistic auditory stimuli condition. The current systems and methods can diagnose good readers versus bad readers and track reading improvement over time.

In some implementations, systems and methods according to the present disclosure can provide a diagnostic for auditory processing disorders including hearing loss. In some implementations, hearing loss and auditory processing disorders may attenuate the sensory evoked response of the natural speech envelope to a naturalistic auditory stimuli. For example, patients with sensorineural hearing loss can have a reduced sensory evoked response amplitude. In some implementations, patients with nerve damage and conduction loss may have a prolonged sensory evoked response latency. In some implementations, the current systems and methods can track the sensory evoked response for patients with deficits in hearing through multiple measurements of the subject's response to a naturalistic sensory stimuli.

In some implementations, systems and methods according to the present disclosure can provide a cognitive diagnostic for multiple sclerosis (MS). Patients with MS have demyelination and axonal injuries, which may result in a delay in the latency of the neural response. In some implementations, the sensory evoked response may be delayed in the MS patients in response to naturalistic speech streams. The sensory evoked response in MS patients may also be delayed to naturalistic visual and somatosensory stimuli. In some implementations, tracking the sensory evoked in MS patients can measure the course of the illness and the relapsing remitting effects. In some implementations, the current systems and methods can compare the efficacy of medical treatments in patients with MS.

In some implementations, systems and methods according to the present disclosure can provide a diagnostic for neuropathy. Neuropathy patients with nerve damage may have a modulated neural representation of the speech envelope. For example, patients with diabetic neuropathy may have an attenuated and delayed sensory evoked response as compared to healthy controls. In some implementations, the current systems and methods can compare the efficacy of medical treatments for patient's neuropathy, as well as tracking the cognitive function of patients over time.

In some implementations, systems and methods according to the present disclosure can provide a diagnostic for Alzheimer's disease, dementias, and other degenerative neurological conditions with cognitive impairments. For example, Alzheimer's patients have more prolonged event-related potentials as compared to mild cognitive impairment patients. Also, dementia may modulate the neural representation of the speech envelope in passive paradigms and working memory paradigms. In some implementations, Alzheimer's and mild cognitively impaired patients may have a delayed latency, modulated amplitude, and an atypical spatial distribution of the envelope response as compared to healthy controls. In addition, the envelope response may index disease severity and progression. Early identification of mild cognitively impaired patients and Alzheimer's patients can allow for a more effective medical intervention and improved pharmaceutical drug development. The current systems and methods can be utilized to track the cognitive function in such patients over the course of their illness.

In some implementations, the systems and methods according to the present disclosure can provide a diagnostic for schizophrenia. Schizophrenia patients may have alterations in the latency and amplitude of the event-related response components as compared to healthy controls. In some implementations, a naturalistic stimuli set that measures the sensory evoked response to a naturalistic sensory stimuli may provide more consistent and robust neural markers for Schizophrenia, which can help diagnose and track the condition over time.

In some implementations, systems and methods according to the present disclosure may provide a diagnostic for HIV related cognitive impairments. HIV positive patients as compared to healthy controls may show a delayed sensory evoked response based on the severity of the HIV virus. In some implementations, the current disclosure can measure the delayed sensory evoked response to the naturalistic sensory stimuli for tracking the cognitive impairment of the patient, and measure the efficacy of medical treatment to treat the cognitive impairments, as disclosed in FIG. 6.

In some implementations, systems and methods according to the present disclosure provide an EEG or ECoG based monitoring of deep brain or transcranial stimulation. In some implementations, the sensory evoked response can measure the real-time effects of brain stimulation. For example, stimulation of language specific cortical areas as a treatment for aphasia and other language disorders can be monitored through the sensory evoked response to naturalistic sensory stimuli as an EEG metric of cortical activation to speech. In some implementations, the envelope response can be correlated with behavioral measures to determine the best parameters such as duration, amplitude or frequency of the signal features of the treatment.

In some implementations, systems and methods according to the present disclosure can provide a diagnostic for monitoring a subject's acquisition of a new language. The sensory evoked response to a continuous natural speech stream can track a subject's acquisition of new languages. In some implementations, a shift in a latency, amplitude, or topography of the sensory evoked response as indicated in an EEG or ECOG cross-correlation with a naturalistic auditory stream of speech in the new language can be indicative of improved familiarity and comprehension in the new language. In some implementations, as a participant learns a new language, the envelope response to the language can be more precise and the spatial distribution of the response can shift to the left-oriented language networks through enhanced deeper left-centered component latencies.

In some implementations, systems and methods according to the present disclosure can be used for prosthetic development. The current systems and methods can be used to improve neural prosthetic development through the continuous measurement of neural-prosthetic coupling in the auditory, visual, and somatosensory modalities. For example, a neural measure of an auditory prosthetic through the sensory evoked response can determine the brain's adaptation to the prosthetic. In some implementations, a shift in a latency, amplitude, or topography of the sensory evoked response as indicated in an EEG or ECoG cross-correlation with an auditory signal processed by an auditory prosthetic can be indicative of improved patient adaptation to the prosthetic.

Figure 7:
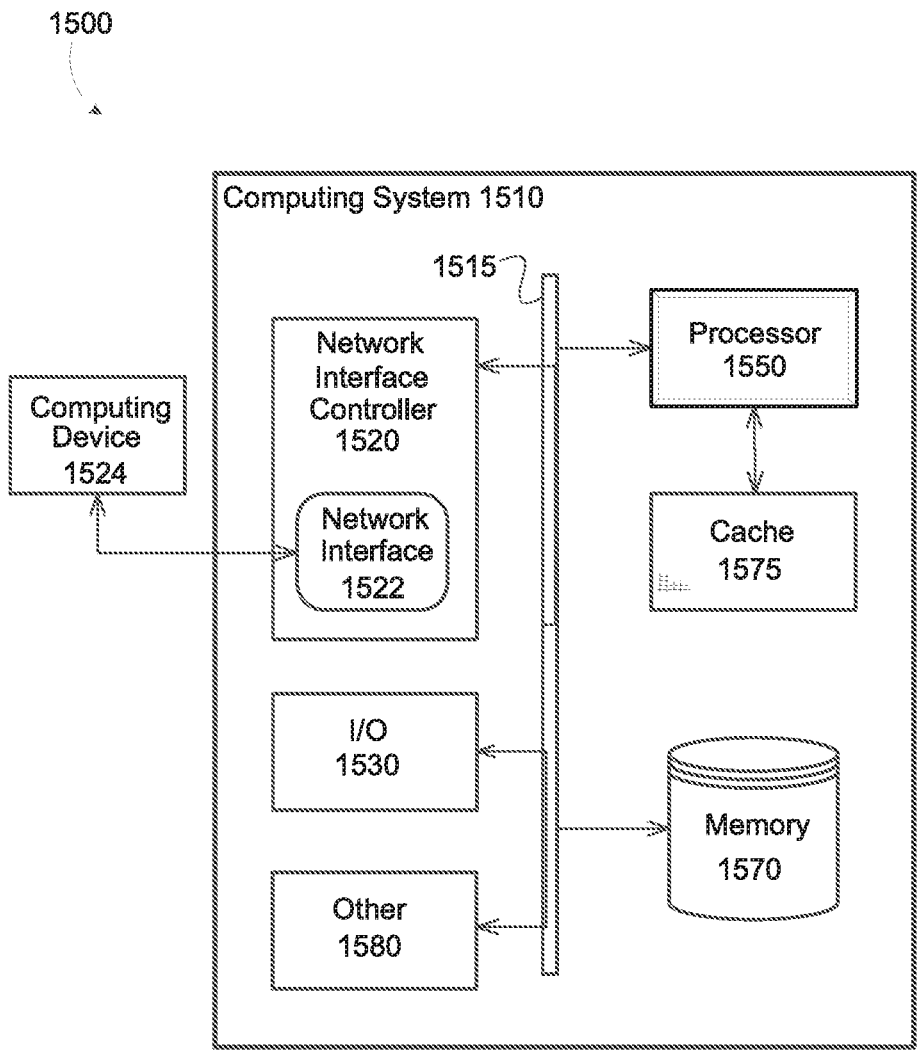
FIG. 7 illustrates a block diagram of an example computing system.

FIG. 7 illustrates a block diagram of an example computing system 1500. In some implementations, the computing system 1500 may be utilized in implementing the diagnostic methods in FIGS. 2 and 7.

In broad overview, the computing system 1510 includes at least one processor 1550 for performing actions in accordance with instructions and one or more memory devices 1570 or 1575 for storing instructions and data. The illustrated example computing system 1510 includes one or more processors 1550 in communication, via a bus 1515, with at least one network interface controller 1520 with network interface ports 1522(a-n) connecting to other computing devices 1524(a-n), memory 1570, and any other devices 1580, e.g., an I/O interface. Generally, a processor 1550 will execute instructions received from memory. The processor 1550 illustrated incorporates, or is directly connected to, cache memory 1575.

In more detail, the processor 1550 may be any logic circuitry that processes instructions, e.g., instructions fetched from the memory 1570 or cache 1575. In many embodiments, the processor 1550 is a microprocessor unit or special purpose processor. The computing device 1500 may be based on any processor, or set of processors, capable of operating as described herein. In some implementations, the processor 1550 can be capable of executing the diagnostic methods shown in FIG. 2 and FIG. 7. The processor 1550 may be a single core or multi-core processor. The processor 1550 may be multiple processors. In some implementations, the processor 1550 can be configured to run multi-threaded operations. In some implementations, the processor 1550 may host one or more virtual machines or containers, along with a hypervisor or container manager for managing the operation of the virtual machines or containers. In such implementations, one or more of the methods 1300 and 1400 shown in FIG. 2 and FIG. 7 can be implemented within the virtualized or containerized environments provided on the processor 1550.

The memory 1570 may be any device suitable for storing computer readable data. The memory 1570 may be a device with fixed storage or a device for reading removable storage media. Examples include all forms of non-volatile memory, media and memory devices, semiconductor memory devices (e.g., EPROM, EEPROM, SDRAM, and flash memory devices), magnetic disks, magneto optical disks, and optical discs (e.g., CD ROM, DVD-ROM, and BluRay® discs). A computing system 1500 may have any number of memory devices 1570. In some implementations, the memory 1570 supports virtualized or containerized memory accessible by virtual machine or container execution environments provided by the computing system 1510.

The cache memory 1575 is generally a form of computer memory placed in close proximity to the processor 1550 for fast read times. In some implementations, the cache memory 1575 is part of, or on the same chip as, the processor 1550. In some implementations, there are multiple levels of cache 1575, e.g., L2 and L3 cache layers.

The network interface controller 1520 manages data exchanges via the network interfaces 1522(a-n) (also referred to as network interface ports). The network interface controller 1520 handles the physical and data link layers of the OSI model for network communication. In some implementations, some of the network interface controller's tasks are handled by the processor 1550. In some implementations, the network interface controller 1520 is part of the processor 1550. In some implementations, a computing system 1510 has multiple network interface controllers 1520. The network interfaces 1522(a-n) are connection points for physical network links. In some implementations, the network interface controller 1520 supports wireless network connections and an interface port 1522 is a wireless receiver/transmitter. Generally, a computing device 1510 exchanges data with other computing devices 1512(a-n) via physical or wireless links to a network interfaces 1522(a-n). In some implementations, the network interface controller 1520 implements a network protocol such as Ethernet.

The other computing devices 1524(a-n) are connected to the computing device 1510 via a network interface port 1522. The other computing devices 1524(a-n) may be peer computing devices, network devices, or any other computing device with network functionality. For example, a first computing device 1524(a) may be a network device such as a hub, a bridge, a switch, or a router, connecting the computing device 1510 to a data network such as the Internet.

The other devices 1580 may include an I/O interface, external serial device ports, and any additional co-processors. For example, a computing system 1510 may include an interface (e.g., a universal serial bus (USB) interface) for connecting input devices (e.g., a keyboard, microphone, mouse, or other pointing device), output devices (e.g., video display, speaker, or printer), or additional memory devices (e.g., portable flash drive or external media drive). In some implementations, a computing device 1500 includes an additional device 1580 such as a coprocessor, e.g., a math co-processor can assist the processor 1550 with high precision or complex calculations.

While this specification contains many specifics, these should not be construed as limitations on the scope of what may be claimed, but rather as descriptions of particular implementations of the subject matter. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

The subject matter of this specification has been described in terms of particular aspects, but other aspects can be implemented and are within the scope of the following claims. For example, while operations are depicted in the drawings in a particular order, this should not be understood as requiring that such operations be performed in the particular order shown or in sequential order, or that all illustrated operations be performed, to achieve desirable results. The actions recited in the claims can be performed in a different order and still achieve desirable results. As one example, the processes depicted that the accompanying figures do not necessarily require the particular order shown, or sequential order, to achieve desirable results. In certain circumstances, multitasking and parallel processing may be advantageous. Moreover, the separation of various system components in the aspects described above should not be understood as requiring such separation in all aspects, and it should be understood that the described program components and systems can generally be integrated together in a single software product or packaged into multiple software products.

The title, background, brief description of the drawings, abstract, and drawings are hereby incorporated into the disclosure and are provided as illustrative examples of the disclosure, not as restrictive descriptions. It is submitted with the understanding that they will not be used to limit the scope or meaning of the claims. In addition, in the detailed description, it can be seen that the description provides illustrative examples and the various features are grouped together in various implementations for the purpose of streamlining the disclosure. The method of disclosure is not to be interpreted as reflecting an intention that the claimed subject matter requires more features than are expressly recited in each claim. Rather, as the claims reflect, inventive subject matter lies in less than all features of a single disclosed configuration or operation. The claims are hereby incorporated into the detailed description, with each claim standing on its own as a separately claimed subject matter.

The claims are not intended to be limited to the aspects described herein, but are to be accorded the full scope consistent with the language claims and to encompass all legal equivalents. Notwithstanding, none of the claims are intended to embrace subject matter that fails to satisfy the requirements of the applicable patent law, nor should they be interpreted in such a way.

What is claimed is:

1. A method comprising:
   receiving, by a processor, a measurement of a cortical neural response of a subject to one or more naturalistic sensory stimuli;
   receiving, by the processor, information related to the one or more naturalistic sensory stimuli, wherein the information includes at least one signal feature of the one or more naturalistic sensory stimuli;
   determining, by the processor, a statistical relationship between the at least one signal feature of the one or more naturalistic sensory stimuli and the measurement of the cortical neural response of the subject, wherein the at least one signal feature is a sensory envelope of the one or more naturalist sensory stimuli, and the statistical correlation is a cross-correlation between the measurement of the cortical neural response of the subject with the sensory envelope and wherein the determining the statistical relationship further comprises bandpass filtering the measurement of the cortical neural response;
   identifying, by the processor, a latency value based on the determined statistical relationship between the at least one signal feature of the one or more naturalistic sensory stimuli and the measurement of the cortical neural response of the subject;
   determining, by the processor, a cognitive function of the subject based on the identified latency value, wherein determining the cognitive function of the subject based on the identified latency value comprises classifying the subject as being in a minimally conscious state, having emerged from a minimally conscious state, being in a vegetative state, being in a cognitive motor dissociation command following state, or as being in a healthy state; and
   outputting, by the processor, the determined cognitive function of the subject.

2. The method of claim 1, wherein the naturalistic sensory stimuli includes at least one of an auditory, visual, or somatosensory stimuli.

3. The method of claim 1, wherein the naturalistic sensory stimuli comprises natural, conversational speech, continuous video, or continuous somatosensory sensations.

4. The method of claim 1, wherein the at least one signal feature is an amplitude envelope of natural speech included within the naturalistic sensory stimuli.

5. The method of claim 1, wherein determining the statistical relationship comprises cross-correlating the at least one signal feature of the naturalistic sensory stimuli with the received measurement of the cortical neural response.

6. The method of claim 1, further comprising tracking the determined cognitive function over time.

7. The method of claim 1, further comprising:
   after determining the cognitive function of the subject, administering a medical treatment to the subject;
   after administering the treatment, receiving, by the processor, a measurement of a second cortical neural response of a subject to one or more second naturalistic sensory stimuli;
   receiving, by the processor, information related to the one or more second naturalistic sensory stimuli, wherein the information includes at least one signal feature of the one or more second naturalistic sensory stimuli;
   determining, by the processor, a second statistical relationship between the at least one signal feature of the one or more second naturalistic sensory stimuli and the measurement of the second cortical neural response of the subject;

identifying, by the processor, a second latency value based on the determined second statistical relationship; and determining, by the processor, a second cognitive function of the subject based on the identified second latency value; and comparing, by the processor, the determined first cognitive function to the determined second cognitive function;

determining, by the processor, an efficacy of the medical treatment based on the comparison; and, outputting, by the processor, the determined efficacy of the medical treatment.

8. The method of claim 1, wherein the bandpass filtering comprises filtering the cortical neural response of the subject in the range of 1-90 Hz.

9. The method of claim 1, wherein the bandpass filtering comprising bandpass filtering the cortical neural response of the subject in the range of 2-30 Hz.

10. A system comprising:
one or more stored naturalistic sensory stimuli configured to evoke a neural response of a subject;
one or more processors implementing a processing unit configured to determine an indication of a cognitive function of a subject to the one or more naturalistic sensory stimuli by:
  receiving a measurement of a cortical neural response of the subject exposed to the one or more naturalistic sensory stimuli;
  determining a statistical relationship between at least one signal feature of the one or more stored naturalistic sensory stimuli and the measurement of the cortical neural response of the subject, wherein the at least one signal feature, received by the one or more processors, is a sensory envelope of the one or more stored naturalistic sensory stimuli, and the statistical correlation is the cross-correlation between the measurement of the cortical neural response of the subject with the sensory envelope, and wherein the determining the statistical relationship further comprises bandpass filtering the measurement of the cortical neural response;
  identifying a latency value based on the determined statistical relationship between the at least one signal feature of the one or more stored naturalistic sensory stimuli and the measurement of the cortical neural response of the subject;
  determining the indication of the cognitive function of the subject based on the identified latency value, wherein determining the indication of the cognitive function of the subject based on the identified latency value comprises classifying the subject as being in a minimally conscious state, having emerged from a minimally conscious state, being in a vegetative state, being in a cognitive motor dissociation command following state, or as being in a healthy state; and,
an output module for outputting the determined indication of the cognitive function of the subject.

11. The system of claim 10, wherein the naturalistic sensory stimuli comprises natural, conversational speech, continuous video, or continuous somatosensory sensations.

12. The system of claim 10, wherein the naturalistic sensory stimuli includes at least one of a naturalistic auditory, visual, or somatosensory stimuli.

13. The system of claim 10, wherein at least one signal feature is an amplitude envelope of natural speech included in the naturalistic sensory stimuli.

14. The system of claim 10, wherein determining the statistical relationship comprises cross-correlating at least one signal feature of the naturalistic sensory stimuli with the received measurement of the cortical neural response.

15. The system of claim 10, further comprising a storage unit and the processing unit is further configured to store the identified latency value in the storage unit for tracking the determined cognitive function over time.

16. The system of claim 10, further comprising:
a first stored naturalistic sensory stimuli and a second stored naturalistic sensory stimuli configured to evoke a neural response of a subject;
one or more processors implementing a processing unit configured to determine an indication of the cognitive function of the subject to one or more naturalistic sensory stimuli by:
  after determining the cognitive function of the subject, administering a medical treatment to the subject;
  after administering the treatment, receiving a measurement of a second cortical neural response of a subject to one or more second naturalistic sensory stimuli;
  receiving information related to the one or more second naturalistic sensory stimuli, wherein the information includes at least one signal feature of the one or more second naturalistic sensory stimuli;
  determining a second statistical relationship between the at least one signal feature of the one or more second naturalistic sensory stimuli and the measurement of the second cortical neural response of the subject;
  identifying a second latency value based on the determined second statistical relationship; and
  determining a second cognitive function of the subject based on the identified second latency value; and
  comparing the determined first cognitive function to the determined second cognitive function;
  outputting the efficacy of the medical treatment based on the comparison.

17. The system of claim 10, wherein the processing unit is configured to bandpass filter the cortical neural response of the subject in the range of 1-90 Hz.

18. The method of claim 10, wherein the processing unit is configured to bandpass filter the cortical neural response of the subject in the range of 2-30 Hz.

19. A method comprising:
receiving, by a processor, a measurement of a cortical neural response of a subject to one or more naturalistic sensory stimuli;
receiving, by the processor, information related to the one or more naturalistic sensory stimuli, wherein the information includes at least one signal feature of the one or more naturalistic sensory stimuli;
determining, by the processor, a statistical relationship between the at least one signal feature of the one or more naturalistic sensory stimuli and the measurement of the cortical neural response of the subject, wherein the at least one signal feature is a sensory envelope of the one or more naturalist sensory stimuli, and the statistical correlation is the cross-correlation between the measurement of the cortical neural response of the subject with the sensory envelope and wherein the determining the statistical relationship further comprises bandpass filtering the measurement of the cortical neural response;
identifying, by the processor, a latency value based on the determined statistical relationship between the at least one signal feature of the one or more naturalistic sensory stimuli and the measurement of the cortical neural response of the subject;
determining, by the processor, a cognitive function of the subject based on the identified latency value, wherein determining the cognitive function of the subject based on the identified latency value comprises at least one of:
  determining a depth of anesthesia; or
  diagnosing one of a speech and language disorder, an auditory processing disorder, a level of Alzheimer's progression, schizophrenia, and a degree of dementia; and
outputting, by the processor, the determined cognitive function of the subject.

* * * * *